(12) United States Patent
Lane et al.

(10) Patent No.: US 7,244,570 B2
(45) Date of Patent: Jul. 17, 2007

(54) METHODS AND COMPOSITIONS FOR MODULATING "MARGINALLY INDISCRIMINANT" HYBRIDIZATIONS

(75) Inventors: Michael J. Lane, Baldwinsville, NY (US); Albert S. Benight, Schaumburg, IL (US); Brian D. Faldasz, Littleton, MA (US)

(73) Assignee: Luminex Molecular Diagnostics, Inc., Toronto (CA)

( * ) Notice: Subject to any disclaimer, the term of this patent is extended or adjusted under 35 U.S.C. 154(b) by 382 days.

(21) Appl. No.: 10/902,049

(22) Filed: Jul. 30, 2004

(65) Prior Publication Data

US 2005/0123903 A1 Jun. 9, 2005

Related U.S. Application Data

(63) Continuation of application No. 09/747,164, filed on Dec. 22, 2000, now abandoned, which is a continuation of application No. 09/534,432, filed on Mar. 23, 2000, now abandoned, which is a continuation of application No. 09/366,085, filed on Aug. 3, 1999, now abandoned.

(60) Provisional application No. 60/095,313, filed on Aug. 4, 1998, now abandoned.

(51) Int. Cl.
  *C12Q 1/68* (2006.01)
  *C07H 21/02* (2006.01)
  *C07H 21/04* (2006.01)

(52) U.S. Cl. .......... 435/6; 536/23.1; 536/24.3

(58) Field of Classification Search ............ 435/6; 536/23.1, 24.3
See application file for complete search history.

(56) References Cited

U.S. PATENT DOCUMENTS

| | | | |
|---|---|---|---|
| 4,870,013 A | 9/1989 | Gelfand et al. |
| 5,008,182 A | 4/1991 | Sninsky et al. |
| 5,079,351 A | 1/1992 | Sninsky et al. |
| 5,268,268 A | 12/1993 | Sninsky et al. |
| 5,527,898 A | 6/1996 | Bauer et al. |
| 5,567,603 A | 10/1996 | De Leys et al. |
| 5,594,122 A | 1/1997 | Friesen et al. |
| 5,594,123 A | 1/1997 | Sninsky et al. |
| 5,599,662 A | 2/1997 | Respess |
| 5,637,455 A | 6/1997 | Henco et al. |
| 5,658,737 A | 8/1997 | Nelson et al. |
| 5,677,147 A | 10/1997 | Henco et al. |
| 5,712,385 A | 1/1998 | McDonough et al. |
| 5,733,781 A | 3/1998 | Ryder et al. |
| 5,756,709 A | 5/1998 | Nelson et al. |
| 5,780,607 A | 7/1998 | Goodnow, Jr. et al. |
| 5,789,538 A | 8/1998 | Rebar |
| 6,027,884 A | 2/2000 | Lane |
| 6,221,589 B1 | 4/2001 | Lane |

FOREIGN PATENT DOCUMENTS

| EP | 269445 | 6/1988 |
|---|---|---|
| EP | 612844 | 8/1994 |
| EP | 617132 | 9/1994 |
| EP | 655501 | 5/1995 |
| EP | 657532 | 6/1995 |
| JP | 01289486 | 11/1989 |
| WO | WO 91/06679 | 5/1991 |
| WO | WO9315226 | 8/1993 |
| WO | WO 97/08183 | 3/1997 |
| WO | WO0008211 A3 | 8/2000 |

OTHER PUBLICATIONS

Manos, M.M., et al. "Use of Polymerase Chain Reaction Amplification for the Detection of Genital Human Papillomaviruses" Cancer Cells 7 1989, pp. 209-214.

Carpenter et al., A Transcriptionally Amplified DNA Probe Assay with Ligatable Probes and Immunochemical Detection, Clinical Chemistry, vol. 39, No. 9, 1993, pp. 1934-1938.

*Primary Examiner*—Ethan Whisenant
(74) *Attorney, Agent, or Firm*—Goodwin Procter LLP

(57) ABSTRACT

The invention relates to the field of molecular biology, nucleic acid chemistry and medical diagnostics. More specifically, it relates to methods and compositions for promoting the hybridization of a nucleic acid probe with a target nucleic acid sequence which is not perfectly matched to the probe.

24 Claims, 9 Drawing Sheets

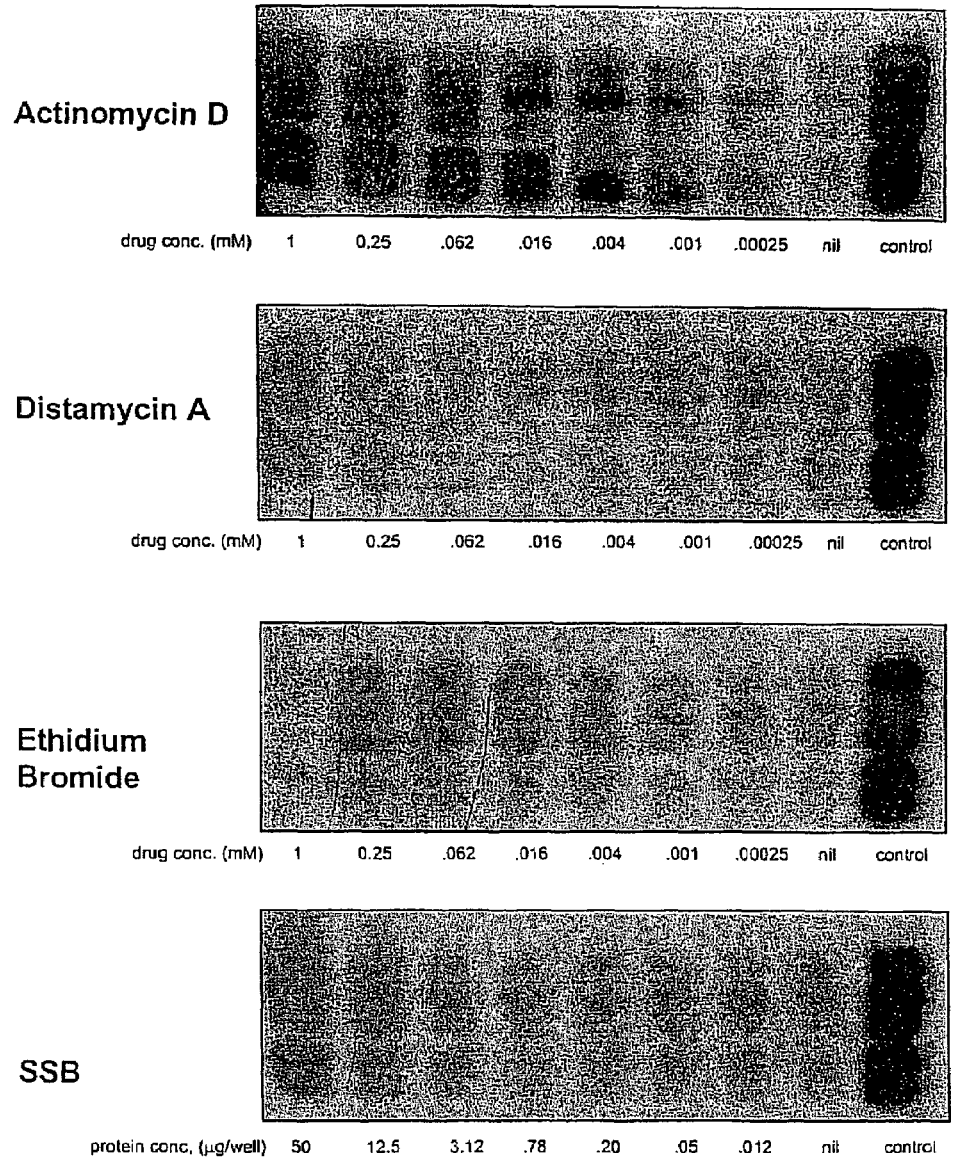
Figure 1. Titration of 4 DNA binders in a DNA hybridization reaction.

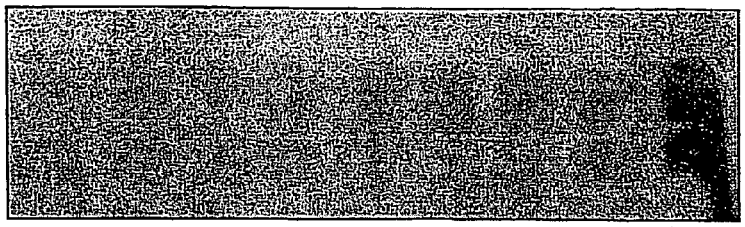
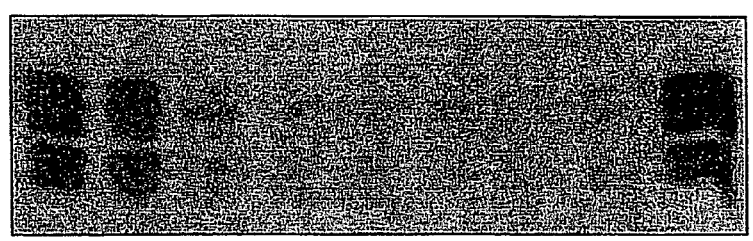
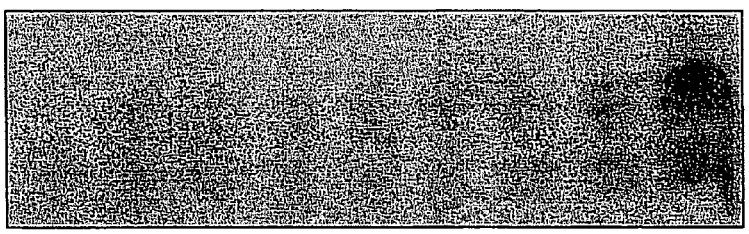
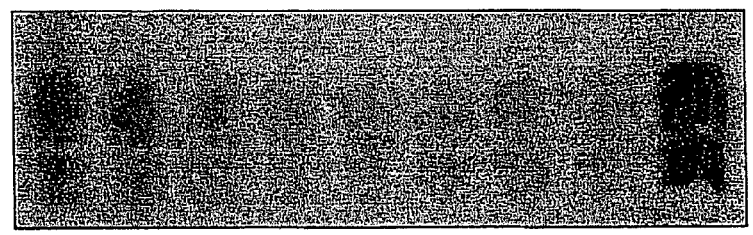
Figure 2. Titration of 4 DNA binder combinations in a DNA hybridization reaction.

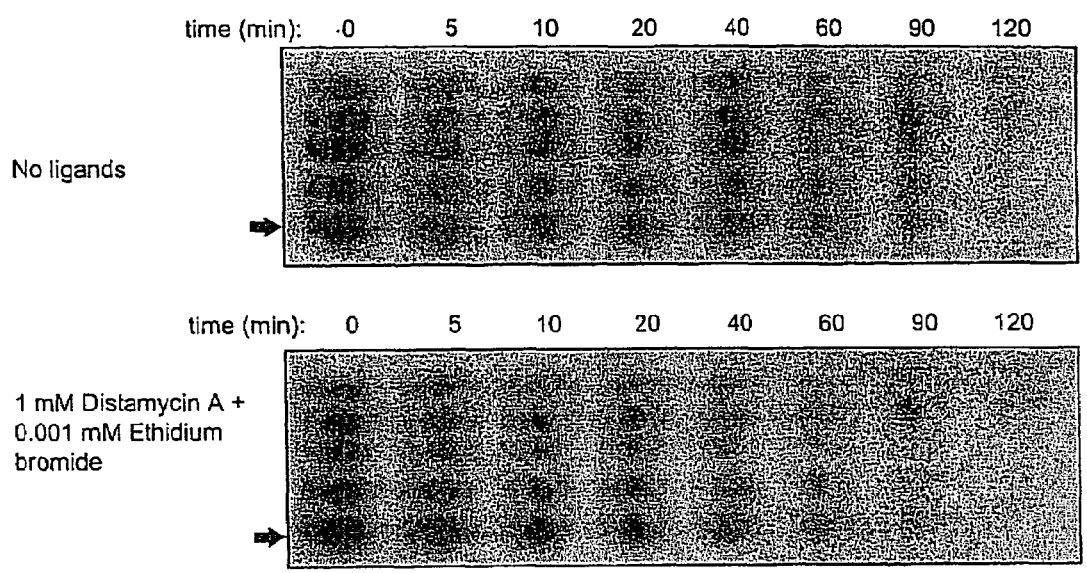
Figure 3a. Time dependence of hybridization in the presence and absence of distamycin A and ethidium bromide.

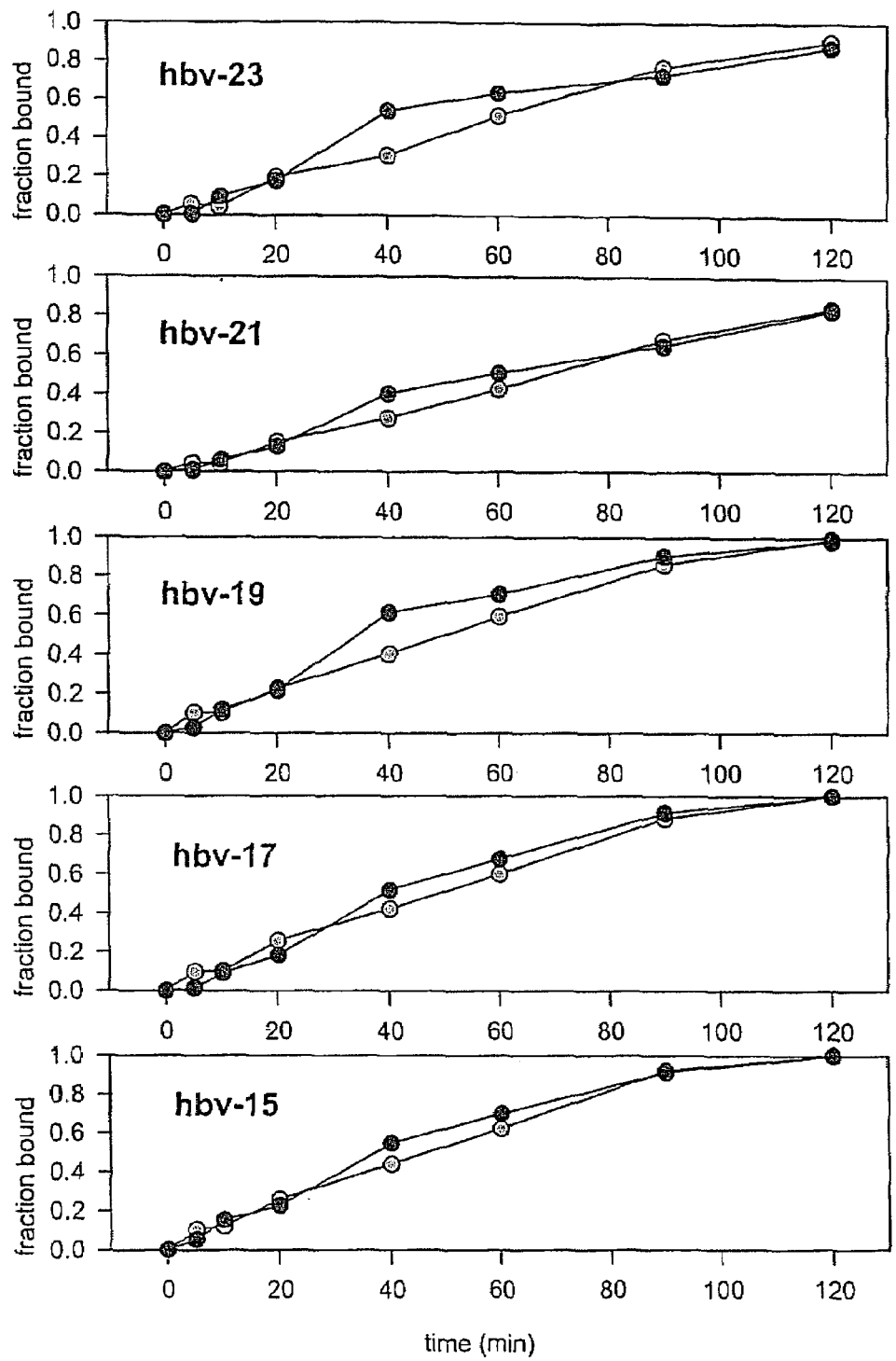
Figure 3b. Plot of normalized binding curves from figure 3.

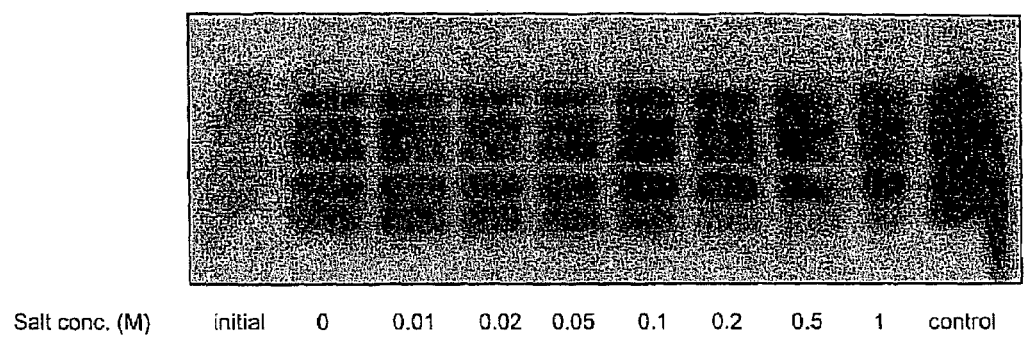
Figure 4. Salt concentration dependence of denaturation at 40% (v/v) formamide.

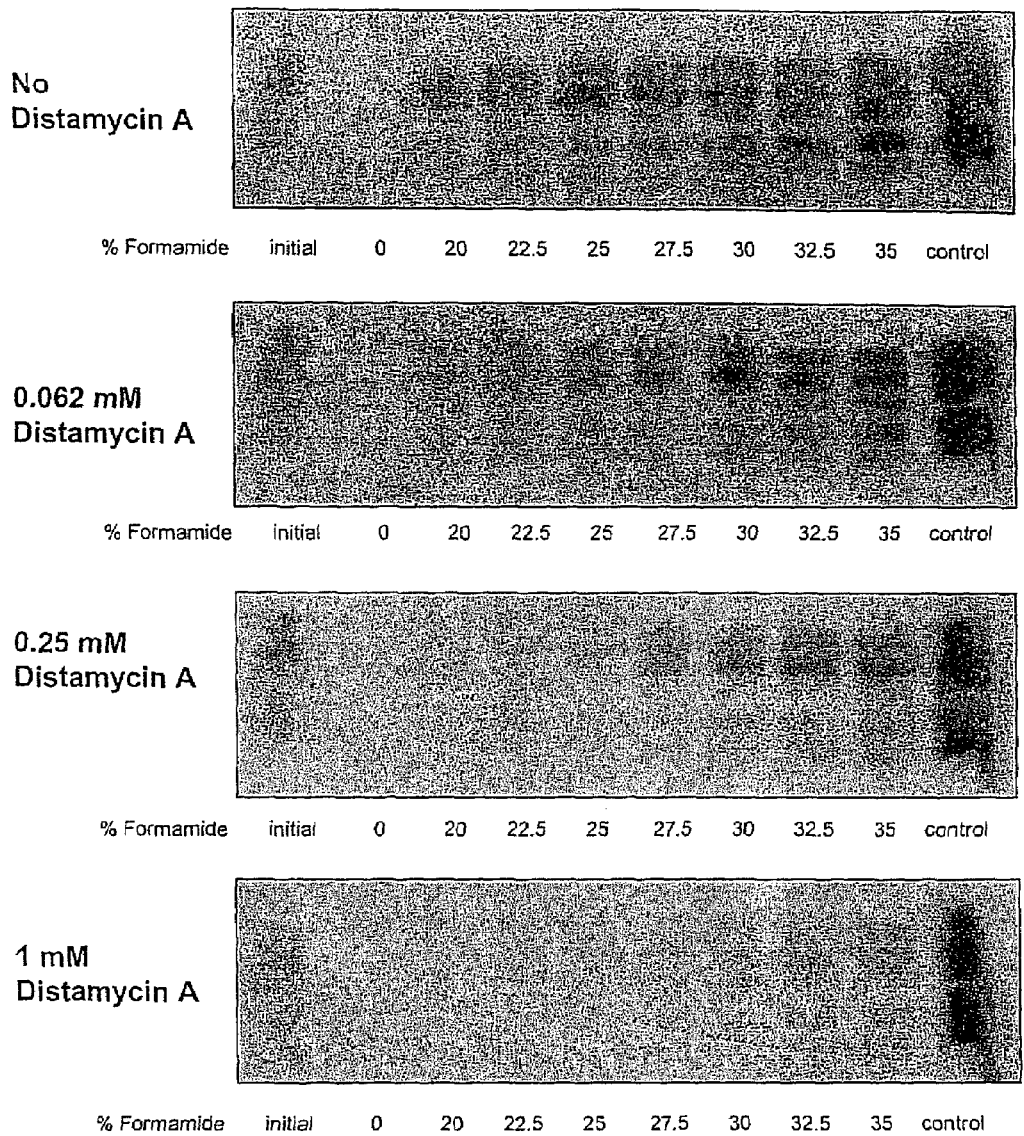
Figure 5a. Formamide concentration is cross-titered with Distamycin A in the wash buffer.

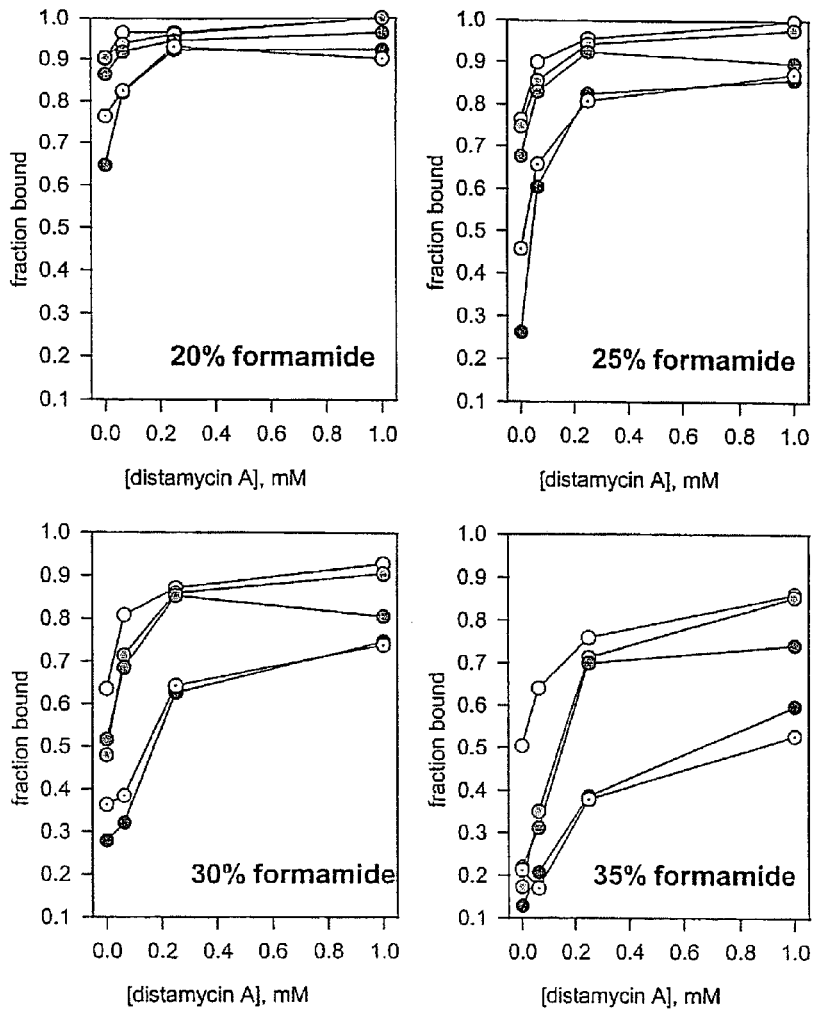
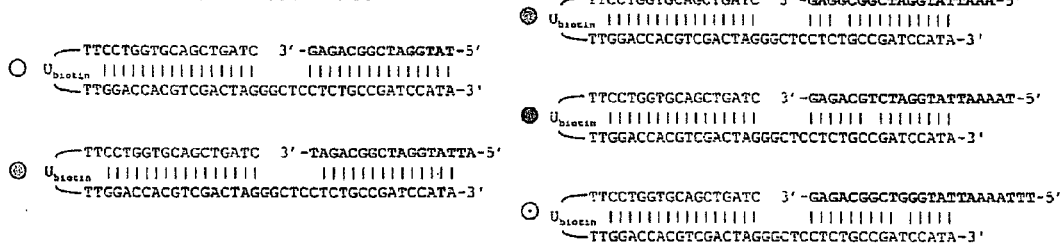
Figure 5b. Fraction of duplex remaining after denaturation as a function of distamycin A concentration at different concentrations of formamide.

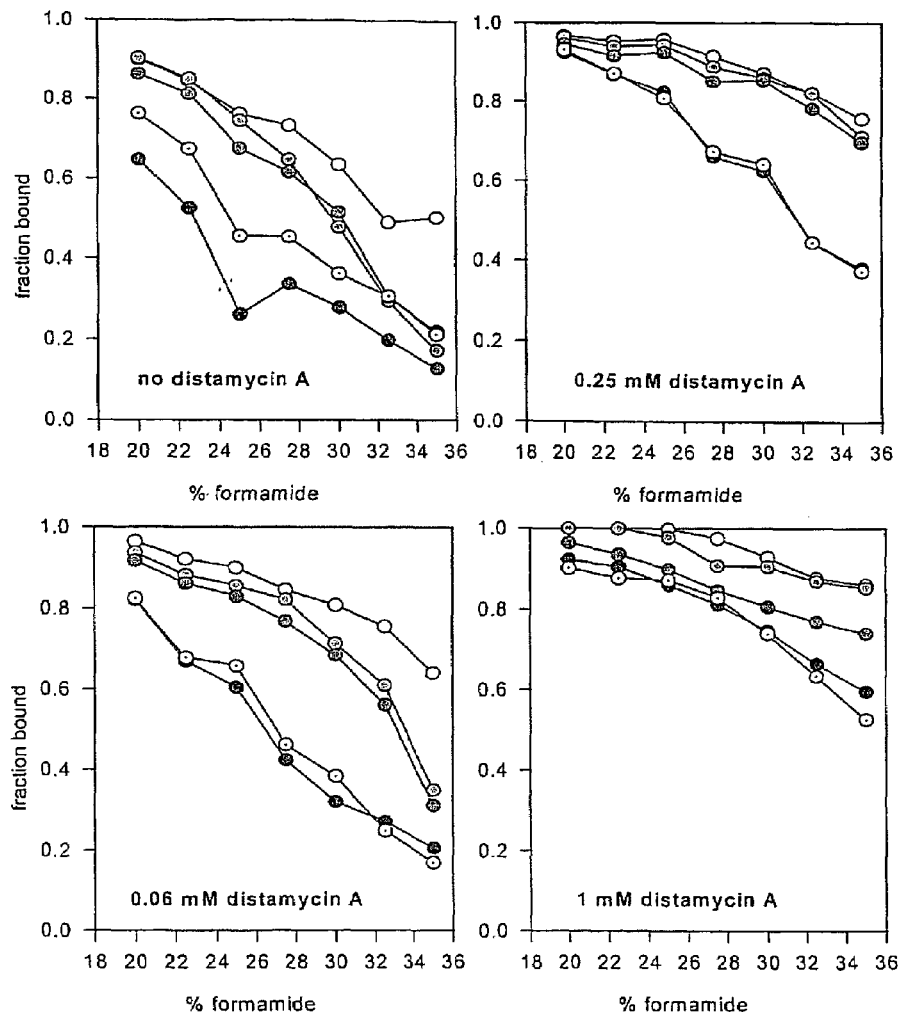
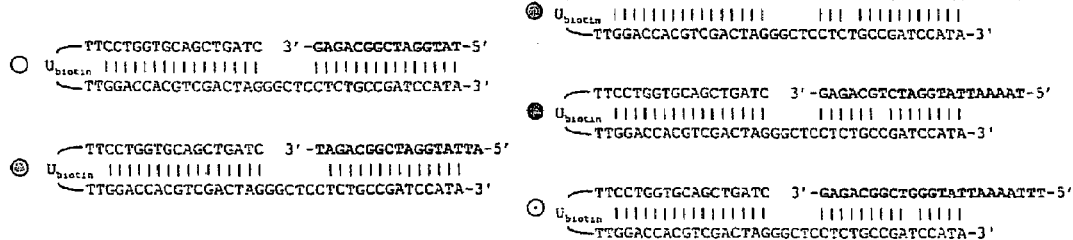
Figure 5c. Fraction of undissociated duplex after denaturation as a function of formamide concentration at different concentrations of distamycin A.

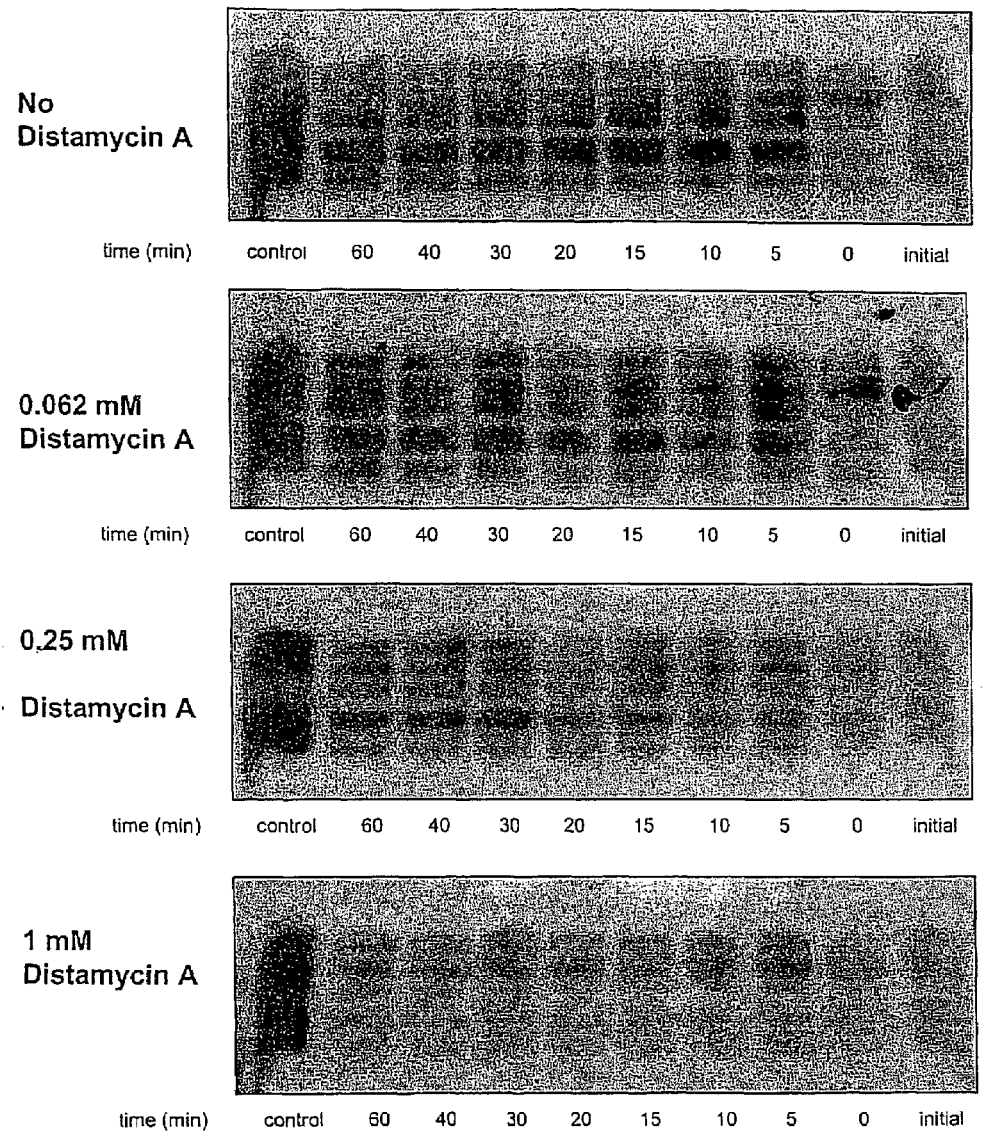
Figure 6. Time dependence of denaturation at 40% (v/v) formamide, as a function of Distamycin A concentration.

SEQUENCE LISTING

<160> NUMBER OF SEQ ID NOS: 6

<210> SEQ ID NO 1
<211> LENGTH: 56
<212> TYPE: DNA
<213> ORGANISM: artificial
<220> FEATURE:
<223> OTHER INFORMATION: Capture Hairpin
<220> FEATURE:

```
<221> NAME/KEY: misc_feature
<222> LOCATION: (19)..(19)
<223> OTHER INFORMATION: Biotinylated Uracil for attaching hairpin to
      solid support

<400> SEQUENCE: 1
ctagtcgacg tggtccttnt tggaccacgt cgactagggc tcctctgcga tccata         56

<210> SEQ ID NO 2
<211> LENGTH: 15
<212> TYPE: DNA
<213> ORGANISM: artificial
<220> FEATURE:
<223> OTHER INFORMATION: target molecule

<400> SEQUENCE: 2
tatggatcgg cagag                                                      15

<210> SEQ ID NO 3
<211> LENGTH: 17
<212> TYPE: DNA
<213> ORGANISM: artificial
<220> FEATURE:
<223> OTHER INFORMATION: target molecule

<400> SEQUENCE: 3
attatggatc ggcagat                                                    17

<210> SEQ ID NO 4
<211> LENGTH: 19
<212> TYPE: DNA
<213> ORGANISM: artificial
<220> FEATURE:
<223> OTHER INFORMATION: Target molecule

<400> SEQUENCE: 4
aaattatgga tcggcggag                                                  19

<210> SEQ ID NO 5
<211> LENGTH: 21
<212> TYPE: DNA
<213> ORGANISM: artificial
<220> FEATURE:
<223> OTHER INFORMATION: Target molecule

<400> SEQUENCE: 5
taaaattatg gatctgcaga g                                               21

<210> SEQ ID NO 6
<211> LENGTH: 23
<212> TYPE: DNA
<213> ORGANISM: artificial
<220> FEATURE:
<223> OTHER INFORMATION: Target molecule

<400> SEQUENCE: 6
tttaaaatta tgggtcggca gag                                             23
```

METHODS AND COMPOSITIONS FOR MODULATING "MARGINALLY INDISCRIMINANT" HYBRIDIZATIONS

CROSS REFERENCE TO RELATED APPLICATIONS

This application is a continuation of U.S. application Ser. No. 09/747,164 filed on Dec. 22, 2000, now abandoned, which is a continuation of U.S. application Ser. No. 09/534,432, filed Mar. 23, 2000, now abandoned, which is a continuation of U.S. application Ser. No. 09/366,085, filed Aug. 3, 1999, now abandoned, which claims priority from U.S. application Ser. No. 60/095,313, filed Aug. 4, 1998, now abandoned.

BACKGROUND OF THE INVENTION

The ability to control hybridization of a nucleic acid strand (a probe) to its complement, while excluding imperfectly base-paired probe hybridization has been central to the advancement of both molecular biological techniques and to design of nucleic acid diagnostic systems. Much attention has been paid to this issue because identification of a particular mutant nucleic acid sequence fully complementary to a probe can permit detection of, for example, the existence of a mutant sequence (genetic disorders) or a particular virulent bacterial or viral strain in a patient. Thus, is studies of the physics of mismatched probe:target energetics has focused on the difference in free energy of such mismatches with the hope that such knowledge will benefit the development of assays in which such mismatches are excluded. For example, in diagnosis of a genetic disorder a mutant probe for targeting a nucleic acid molecule having a sequence containing a single base mismatch associated with such a disorder would produce a false positive result if the probe also hybridizes to the wild-type (unmutated) sequence. In other words, the assay must be sufficiently discriminatory in order for the probe to bind to the molecule having the mutated base and not to the molecule lacking the mutated base. If the probe hybridizes to both molecules, then the hybridization result would indicate the presence of the single base mutated sequence even though it was not, in fact, contained in the tested sample. In general, the environment of the reaction is manipulated to eliminate such mismatch probe:target interactions by modifying the physical conditions for hybridization (e.g., temperature and or time) or composition of the hybridization buffer (e.g., salt, divalent ions denaturing agents, etc.).

On the other hand, however, it is advantageous, in some applications, to have a probe which is known to hybridize with molecules containing particular mismatched sequences (a "marginally indiscrimninant" probe) within a desired degree of homology to the probes' perfect complement. This would permit a single probe to be used in an assay for determining the presence of nucleic acid molecules containing any of the mismatched sequences. Such an assay would thus reduce, or possibly even eliminate, the need for more than one probe, each containing a nucleic sequence precisely corresponding to a sequence of a target molecule. Achievement of such a probe could be useful as a "multiplex" (multiple assays from one probe) probe. To date, for example, conventional multiplexing has relied upon the inclusion of multiplex specific probes into one cocktail reaction (e.g., multiplex polymerase chain reaction (PCR)), rather than just one probe.

There are always going to be constraints on an indiscrimninant probe. It would be generally acceptable for a probe to hybridize to any nucleic acid molecule whether complementary or not (although there may be limited use for such a probe in detecting the presence or absence of any DNA). This type of probe and/or conditions for hybridization of the probe would detect even sequences which shared no homology with the probes' complement. At the other end of the spectrum, it is desirable that when designing a marginally indiscrimninant probe for detecting viral nucleic acid sequences, for example, to design a probe such that a single probe will pick up all known of sequence within a limited degree of homology (say 10, 20, 30, 40 or 50% homology).

There are known approaches for detecting target nucleic acids by hybridization of a probe having a nucleic acid sequence fully complementary to or substantially complementary to a sequence of a target nucleic add. Methods have thus been developed to detect viral nucleic acid sequences and their variants by hybridization using probes fully complementary to or substantially complementary to the viral nucleic acid sequences, as exemplified by U.S. Pat. Nos. 5,008,182; 5,079,351; 5,268,268; 5,567,603; 5,594,122; 5,594,123; 5,599,662; and 5,733,781, the text of which is incorporated herein by reference.

The specifications of these patents disclose methods and compositions of nucleic acids for as probes for detecting nucleic acid sequences of the family of Human T-cell Leukemia Viruses (HTLV) and the Human Immunodeficiency Virus (HIV). HIV and its variants are thought to be responsible for the acquired immunodeficiency syndrome (AIDS). The probes and methods disclosed in these patents for detecting the presence or absence of the viral DNA utilize probes to conserved regions of these viruses, but the disclosed approaches have limited applicability. This is because of the now well-known genetic variability of human immunodeficiency viruses. Genetic variations arise with high frequency. This variability has complicated the development of assays for detecting the presence of their genetic material. Further, while a comparison of various HIV-1 isolates has revealed, regions of the genome that are reasonably well conserved, it is possible that even the conserved regions, regions to which the probes have been designed to hybridize, may at mutate in the future. If so, probes designed for detecting the conserved regions may not hybridize to the one is conserved region as a result of base mismatches.

As a further example, U.S. Pat. No. 5,567,603 describes probes for detecting HIV-3 that hybridize neither with the sequences of HIV-1 nor with the sequences of HIV-2 under stringent hybridization conditions. Thus, the ability to design a single nucleic acid probe and a method that will allow hybridization of the probe to all HIV strains and their variants but not to other non-target partially complementary nucleic acid sequences or other non-related viral nucleic acid sequences would have advantages over current approaches.

SUMMARY OF THE INVENTION

The present invention describes how a nucleic acid probe with mismatches to a target may be forced to hybridize to a target without hybridizing indiscriminantly with other non-target partially complementary nucleic acids. The methods of the invention require that nucleic acid duplex ligands as well as nucleic acid single-strand ligands be titered in concentration against one another to achieve the required degree of mismatch target hybridization without obtaining non-target hybridization.

In one aspect of the invention, a method of providing a nucleic acid molecule for potential use as a probe for a family of nucleic acid molecules in the presence of a nucleic acid sequence binding ligand which will promote hybridization of the probe to all the members of the family of target sequences and not to non-target partially complementary sequences, is provided. The method includes the steps of providing the family of first nucleic acid molecules wherein each member of the family is related to all other members of the family by a consensus sequence. A second nucleic acid molecule complementary to the consensus sequence is synthesized by methods well known in the art. It is highly preferable that the homology of this complementary sequence to other viral nucleic acid sequences as well as other sequences in general be determined by comparing its nucleotide sequence against those listed in a database (e.g., GenBank, DDBJ, EBI, or GSDB) to ensure that it does not by chance happen to have significant homology to other non-target partially complementary sequences. In addition, the homology of the complementary sequence should also be searched against all members of the family of target sequences to determine if the probe might hybridize to a region(s) other than it was originally intended to. Once it is determined that the complementary sequence will most likely not hybridize to a region(s) of the target sequence and all its family members other than it was intended to or to other non-target partially complementary nucleic acid sequences, the nucleic acid sequence complementary to the consensus sequence can be used as a probe. The ability of the probe to hybridize to the consensus region of the target nucleic acid sequence and all members of the family is then determined in the presence of a certain concentration of nucleic acid sequence binding ligand known to affect hybridization of the probe to the complementary region of the target sequence. This is repeated at several different concentrations of ligand, such that the concentration of ligand at which the probe is able to bind to the target nucleic acid sequence and all its family members equally well without affecting the hybridization of the probe to other non-target partially complementary nucleic acid sequences is the concentration of ligand that will be used for subsequent methods of the invention for that particular probe in detecting the presence of the its target nucleic acid sequence and its genetic variants.

In yet another aspect, hybridization of the probe to the target nucleic acid sequence and its family members can be further improved in the presence of two different nucleic acid binding ligands.

In a preferred embodiment, a method of promoting the hybridization of a nucleic acid capture moiety comprising a nucleic acid sequence complementary to a consensus sequence of a target single-stranded nucleic acid sequence and all its family members without hybridizing to a plurality of other non-target partially complementary nucleic acid sequence suspected of being present in a sample is provided. The method includes the steps of identifying at least one consensus sequence to a region of the target duplex nucleic acid sequences and all its genetic variants suspected of being present in a sample; synthesizing a nucleic acid sequence complementary to the consensus sequence (probe); providing a nucleic acid capture moiety comprising the probe; a nucleic acid binding ligand, wherein the ligand has been selected to promote hybridization of the probe to the corresponding complementary region of the target nucleic acid and all its family members; the sample suspected of containing the target nucleic acid sequence and all its family members; and allowing the target single-stranded nucleic acid sequence and all its family members to hybridize to the nucleic acid capture moiety comprising the probe, without promoting the hybridization of other non-target partially complementary nucleic acid sequences to the nucleic acid capture moiety.

In yet another preferred embodiment, a consensus sequences of the target sequence and all its family members can be amplified by PCR if it is suspected that direct detection of the target nucleic acid sequences and all its family members may be difficult or impossible. In this case, the nucleic acid primers used for detecting the target nucleic acid sequences and all its family members should be designed such that the primers will allow amplification of the region of target nucleic acid sequence and all its family members (i.e., the consensus sequence) to be detected without simultaneous amplification of non-target partially complementary nucleic acid sequences from other viral nucleic acid sequences or human genomic nucleic acid sequences. The hybridization of the amplified region of the target sequence and all its family members to a nucleic acid capture moiety comprising the probe can then be performed under conditions in which the presence of a nucleic acid sequence binding ligand will promote hybridization of the target single-stranded nucleic acid sequence and all its family members to the nucleic acid capture moiety without promoting the hybridization of other non-target partially complementary nucleic acid sequences.

In a preferred embodiment, the invention described herein can be used to detect nucleic acid sequences of the AIDS virus and all of its family members without detecting other non-target viral nucleic acid sequences or human genomic DNA.

In yet another preferred embodiment, the invention described herein can be used to detect nucleic acid sequences associated with infectious diseases, genetic disorders, or cellular conditions such as cancer in which the gene responsible for the pathological condition is known to be caused by several mismatch variant nucleic acid sequences. Examples of such genes include but are not limited to p53, ras, BRCA1, BRCA2, or APC.

In another embodiment, the invention herein relates to a multi-container kit for detecting target nucleic acid sequences and their mismatch nucleic acid sequences suspected of being present in a sample, which kit comprises:

(a) a nucleic acid capture moiety comprising a labeled probe nucleic acid sequence substantially complementary to a consensus sequence of the target duplex nucleic acid sequence and all its family members variants suspected of being present in a sample; and (b) at least one nucleic acid sequence binding ligand, wherein the ligand promotes hybridization of the target single-stranded nucleic acid sequence and all its family members to the nucleic acid capture moiety comprising the labeled probe sequence without promoting the hybridization of other non-target partially complementary nucleic acid sequences.

Preferably, the kit also contains nucleic acid sequences primers for amplifying the region of the target nucleic acid sequence and all its family members to be detected, an agent for polymerization and four different nucleosides. It is also preferable that the kit contain the relevant positive and/or negative controls.

In preferred embodiments, the label of the labeled probe nucleic acid sequence is then selected from the group consisting of antibody, antigens, radioisotopes, fluorescent, enzyme, lecithin or biotin.

In a preferred embodiment, the components of the kit are designed to detect the AIDS virus and all its family members without detecting non-target viral nucleic acid sequences and other non-target nucleic acid sequences.

In another preferred embodiment, the components of the kit are designed to detect nucleic acid sequences associated with infectious diseases, genetic disorders, or cellular conditions such as cancer in which the gene responsible for the pathological condition is known to be caused by several mismatch variant nucleic acid sequences. Examples of such genes include but are not limited to p53, ras, BRCA1, BRCA2, or APC.

BRIEF DESCRIPTION OF THE FIGURES

FIG. 1 shows the effect of titrating of four DNA binding ligands in a DNA hybridization reaction in which the target molecules were labeled with the radioisotope $^{32}P$. Dark bands indicate unbound target (i.e., higher band intensity=less bound target). The control lane shows the total intensity of unbound target. Hybridization was allowed to occur under the conditions described herein. At the end of the specified time period for hybridization, the amount of unbound target was determined by gel electrophoresis.

FIG. 2 shows the effect of titrating combinations of four DNA binding ligands in a DNA hybridization reaction in which the target molecules were labeled with $^{32}P$. Distamycin A was held constant at 1 mM for those sets with drug combinations. Hybridization was allowed to occur under the conditions described herein. At the end of the specified time period for hybridization, the amount of unbound target was determined by gel electrophoresis.

FIG. 3a shows the time dependence of target-probe hybridization in the presence and absence of distamycin A and ethidium bromide. The arrow indicates the perfect matched probe. At the end of the specified time period amount of unbound target was determined by gel electrophoresis.

FIG. 3b shows graphs of normalized binding curves from the data obtained in FIG. 3a. Gray circles indicate hybridization without DNA ligands. Black circles indicate hybridization in 1 mM distamycin and 0.001 mM ethidium bromide.

FIG. 4 shows the effect of salt concentration dependence of denaturation of target:probe hybrids of 40% (v/v) formamide. The buffer was 10 mM phosphate, pH 7.2 and the specified concentration of NaCl. Wash incubation time was held constant at 1 hr. The amount of unbound target at the end of the wash incubation time was determined by gel electrophoresis.

FIG. 5a shows the effect of formamide concentration when cross-titred with distamycin A in the wash buffer on denaturation of target probe hybrids. Darker bands indicate a higher degree of dissociation. At the end of the wash period, the amount of $^{32}P$ labeled target was determined by gel electrophoresis.

FIG. 5b shows graphs of binding curves from the data obtained in FIG. 5a with each of the constructs shown.

FIG. 5c shows graphs of the fraction of target:probe hybrids remaining after denaturation as a function of formamide at different concentrations of distamycin A with each of the constructs shown.

FIG. 6 shows the extent of dissociation over time as a function of distamycin A concentration in the wash buffer. The formamide concentration was kept constant at 40% (v/v), and distamycin A was titered in 4-fold increments, at 0.062 mM, 0.25 mM, and 1 mM. Time points were from 0 (wash buffer was added and pulled out) to 60 minutes.

DETAILED DESCRIPTION OF THE INVENTION

The methods and unique compositions of the invention are useful in the detection of nucleic acid sequences and all related family members without detecting non-target partially complementary nucleic acid sequences. The methods of the invention can be performed with nucleic acid capture moieties immobilized on a solid support such as multi-well plates, membranes or gene chips. The methods of the invention can also be automated, in part, to speed screening and improve economy.

The term "single-stranded nucleic acid", as used herein, refers to a duplex nucleic acid which has been denatured resulting in two single-stranded nucleic acid sequences of DNA or RNA. Methods of denaturing duplex nucleic acid sequences are well known to those skilled in art. Single-stranded nucleic acid can also mean a mixed DNA-RNA strand, or nucleic acid-like compounds such as peptide nucleic acids. A nucleic acid strand can also include modified (e.g., chemically or biochemically modified) DNA or RNA bases, of which many are known in the art.

The terms "target nucleic acid sequence", "target nucleic acid" or "target strand" refer to a nucleic acid sequence which is to be detected, sequenced, immobilized, or manipulated. The target nucleic acid sequence can be any nucleic add strand, as defined above, and in general will be single-stranded or will be made single-stranded by methods known to those skilled in the art. The target nucleic acid sequence can be obtained from various sources including plasmids, viruses, bacteria, fungi, yeast, plants, and animals, including humans or the target nucleic acid sequence can be obtained from non-natural sources. The target nucleic acid sequence can be obtained from various organisms or tissues, including fluids such as blood, semen, urine and the like. The target nucleic acid sequence is preferably extracted or purified to remove or reduce contaminating or interfering materials such as proteins or cellular debris. Procedures for such purification or extraction of target nucleic acids sequences are known in the art, including, for example, those described in Maniatis et al., *"Molecular Clorung: A Laboratory Manual"*, Cold Spring, Harbor Laboratory (1989), or in Bell et al., *Proc. Nat Acad. Sci. USA* (1991), 78:5759–576. The methods and compositions of the inversion are particularly useful in the detection of nucleic acid sequences associated with infectious diseases, genetic disorders, or cellular conditions such as cancer.

In one aspect, the invention features a nucleic acid capture moiety which has at least one nucleic acid sequence complementary to at least one consensus sequence of a target nucleic acid sequence and having at least two nucleic acid sequence regions which are capable of forming an intramolecular duplex. The capture moiety can be immobilized on the solid support before, simultaneous with, or after capturing the single-stranded target nucleic acid sequence. A nucleic acid capture moiety can "capture" a target nucleic acid sequence by hybridizing to the target nucleic acid sequence and thereby immobilizing the target nucleic acid sequence and all its family members. In preferred embodiments, the nucleic acid capture moiety comprises a nucleic acid sequence strand which has at least one nucleic acid sequence which is complementary to a consensus sequence of the target nucleic acid and all its family member. One example of a nucleic acid capture moiety is a nucleic acid hairpin. A "hairpin" is a double-helical region in a single DNA or RNA strand formed by the hydrogen bonding between adjacent inverse complementary sequences along the nucleic acid strand. The use of a nucleic acid hairpin as a nucleic acid capture moiety has been described in detail in U.S. Pat. No. 5,770,365 issued to the current applicants, the disclosure of which is incorporated herein by reference. In certain embodiments, the nucleic acid sequence capture moiety, whether a single-stranded nucleic acid sequence or a nucleic acid hairpin, may be labeled as with, e.g., a radioisotope, a fluorescent moiety, an antibody, an antigen, a lecithin, an enzyme, biotin or other labels well known in the art. Alternatively, the target sequence may also be labeled or labeled secondary probes may be employed. A "secondary probe" is a nucleic acid sequence which is fully complementary or substantially complementary to a region of the target nucleic acid sequence or to a region of the nucleic acid capture moiety. "Substantially complementary" as used herein means that the sequence must be sufficiently complementary to the nucleic acid being detected such that hybridization will take place under the conditions employed. Alternatively, a nucleic acid capture moiety can also be a linear nucleic acid sequence such as a single stranded DNA or RNA nucleic acid comprising at least one nucleic add sequence, which sequence is complementary to the consensus sequence of all members of the family of target sequences.

As used herein, the term "consensus sequence" means an idealized sequence that represents the nucleotides most often present at each position in a given segment of all members of the family of target sequences. One method of determining a consensus sequence is to use a computer program to compare the target nucleic acid sequence and all its family member sequences for which a consensus sequence is desired. For this purpose, a commercial program with the underlying computer algorithm provided by the National Biomedical Research Foundation using a dot matrix may be conveniently employed. The program involves inputting the nucleic acid sequences of the target nucleic acid sequence and all its generic variants and defining a window size for base pair homology. The program employs graphics to compare the sequences on different axes, and a dot appears where there is at least substantial homology. As used herein, the term "target nucleic acid sequence and all its genetic variants" refers to the wild-type nucleic acid sequence and all base mismatch variants of the wild-type sequence. Once the consensus sequence has been determined a nucleic acid sequence complementary to the consensus sequence is synthesized by methods well known in the art. It is preferable, however, that prior to synthesizing the complementary sequences, the complementary sequence be searched against a plurality of nucleic acid sequences listed in one or more of the nucleic acid sequence databases which include but is not limited to the DNA Data Bank of Japan (DDBJ), the European Bioinformatics Institute (EB), GenBank, or the Genome Sequence Database (GSDB) to determine if the complementary sequence has significant homology to other non-target partially complementary nucleic acid sequences. If the consensus sequence happens by chance to have significant homology to another non-related viral nucleic acid sequence or to an unrelated human sequence, a new consensus sequence to another region of all members of the family of target sequences can be selected and the above process repeated. By doing this, false positives can be eliminated. It is also preferable that the complementary sequence be searched against all members of the family of target sequences to determine if the complementary sequence might hybridize to a region(s) other than it was originally intended to. Once it is determined that the complementary sequence will most likely not hybridize to a to a region(s) of the target sequence and all its family members other than it was intended to or to other non-target partially complementary nucleic acid sequences, the nucleic acid sequence complementary to the consensus sequence can be synthesized and used as a probe. Otherwise, a new consensus sequence should be selected and the above process repeated.

"Sequence identity or homology", as used herein, refers to the sequences similarity between two nucleic acid molecules. When a position in both of the two compared sequences is occupied by the same base, e.g., if a position in each of two DNA molecules is compared by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same, then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from deletions or insertions in one of the sequences are counted as mismatches.

The comparison of sequences and determination of percent homology between is two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htupla=2, Gap penalty=5, Window=4 and Diagonal saved=4. For protein alignments, the pairwise alignment parameters can be Ktuple=1, Gap penalty=3, Window=5, and Diagnosis Saved=5.

Additional non-limiting example of a mathematical algorithm utilized for the comparison of sequences is the algorithm of Karlin and Altachu (1990) Proc. Natn. Acad. Sci. USA 87:2264–68, modified as in Karlin and Altachu (1993) Proc. Natn. Acad. Sci. USA 90:5873–77. Such an algorithm is incorporated into the NBLAST and XBLAST programs (version 2.0) of Altachu, et al., (1990) J. Mol Biol. 215: 403–10. BLAST nucleotide searches can be performed with the NBLAST program, score=100 wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altachu et al., (1977) Nucleic Acids Research 25(17):3389–3402. When utilizing BLAST and Gapped GLAST programs, the default parameters of the respective programs (e.g., XBLAST and NBLAST) can be sued. See http://www.nebi.nlm.nih.gov. Another preferred non-limit ing example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing ALIGN program for comparing amino acid sequences, a PAM120 weight residue table, a gap length penalty of 12, and a gap penalty of 4 can be used.

The compositions and methods of the invention generally feature the use of at least one base-preferring binding ligand (or, in some cases, sequence-specific ligand) to promote hybridization of a probe nucleic acid sequence to the target single-stranded nucleic acid sequence and all its family members without promoting hybridization of other non-target partially complementary nucleic acid sequences. The methods and compositions of the invention can also include one or more additional binding ligands, which can be base-preferring or sequence-specific ligands, or non-specific ligands, and can bind duplex nucleic acid sequences or single-stranded nucleic acid sequences. The term "nonspecific binding ligand", as used herein, refers to a nucleic acid binding ligand that does not substantially preferentially bind to nucleic acid sequences in which one or more specified bases predominate. That is, a "nonspecific binding ligand" binds to all, or a large variety of, bases or sequences approximately equally well. The choice of appropriate ligands will be routine to the skilled artisan in light of the teachings herein, as explained in more detail below.

Ligands suitable for use in the present invention are capable, in general, of binding to nucleic add single strands and/or duplexes. In general, it is necessary to provide at least one base-preferring ligand in the reaction mixtures of the invention.

A variety of base-preferring ligands have been described. For example, the duplex-binding ligand distamycin A has been reported to bind preferentially to AT-rich sequences. Other base-preferring, duplex-binding ligands include certain restriction enzymes, drugs such as actinomycin D (which has a primary binding site of 5'-GC-3', and a secondary preference for GT sites) and intercalators such as ethidium bromide (as described below).

Similarly, base-preferring single strand-binding ligands can be employed in the invention.

The method of the invention is particularly useful for detecting genetic variants of a target nucleic acid sequence by hybridization using a single probe in the presence of a pre-selected nucleic acid binding ligand under conditions such that the nucleic acid binding ligand will promote hybridization of the target nucleic acid and all its genetic variants with the probe but not to other non-target partially complementary nucleic acid sequences. Specifically, the method of the invention can be used to detect the presence of the AIDS virus nucleic acid sequence and all its genetic variants. A candidate consensus sequence to a particular region of the viral nucleic acid sequence and all its family members is first selected. A second nucleic acid sequence complementary to the consensus sequence, the probe, can then be synthesized by methods well known in the art. It is preferable that the nucleic acid sequence of the probe be compared to a plurality of nucleic acid sequences in a database to rule out the possibility that other non-related viral nucleic acid sequences or other nucleic acid sequences with significant homology may hybridize to the probe, resulting in false positives. The conditions under which a nucleic acid ligand will promote hybridization of the probe sequence to the AIDS virus nucleic acid sequence and all its family members is then determined. A second nucleic acid ligand different from the first can also be used to further improve hybridization of the probe to the AIDS virus nucleic acid sequence and all its genetic variants without promoting hybridization of the probe to other non-target partially complementary sequences. If it is suspected that the amount of AIDS viral nucleic acid sequence present is below the level of direct detection of the method herein, the consensus sequence van be amplified by PCR using consensus sequence primers immediately adjacent to the region to be detected.

Similarly, the method of the invention can be used to detect the presence of any nucleic acid sequences associated with infectious diseases, genetic disorders, or cellular conditions such as cancer in which the gene responsible for the pathological condition is known to be caused by several mismatch variant nucleic acid sequences. Examples of such genes include but are not limited to p53, ras, breast cancer antigen 1 (BRCA1), or breast cancer antigen (BRCA2).

The present invention will now be illustrated, but is not intended to be limited by the following examples:

General Methods

A. Constructs Used

The biotinylated DNA capture hairpin (hairpin), SEQ ID NO: 1, was purchased from a commercial supplier (Oligos Therapeutics), with the following structure:

```
    TTCCTGGTGCAGCTGATC-5'
   /
  U*
   \
    TTGGACCACGTCGACTAGGGCTCCTCTGCGATCCATA-3'
```

The duplex region will henceforth be referred to as the "stem." The 5 bases forming a single-stranded loop on one end of the hairpin will be referred to as the "hairpin loop" or "loop." "U" refers to biotinylated U, used for attaching the hairpin to a solid support (in this case, streptavidin-coated microtiter plates). The single-stranded region (shown above in bold-face) will be referred to as the "dangling end."

Single-stranded DNA molecules fully or partially complementary to the dangling end (referred to as "probe") were also purchased from the same supplier. These molecules were of different lengths to allow them to be separated and visualized by PAGE. The sequences are:

| | | |
|---|---|---|
| 15-mer perfect match: | SEQ ID NO: 2 | 5'-TAT GGA TCG GCA GAG-3' |
| 17-mer mismatch: | SEQ ID NO: 3 | 5'-AT TAT GGA TCG GCA GAT-3' |
| 19-mer mismatch: | SEQ ID NO: 4 | 5'-AAAT TAT GGA TCG GCG GAG-3' |
| 21-mer mismatch: | SEQ ID NO: 5 | 5'-TAAAAT TAT GGA TCT GCA GAG-3' |
| 23-mer mismatch: | SEQ ID NO: 6 | 5'-TTTAAAAT TAT GGG TCG GCA GAG-3' |

Note that the mismatches are longer than the 15-mer perfect-matched sequence on the 5'-end.

The duplex molecules formed are:

```
1.    TTCTGGTGCAGCTGATC-5'  GAGACGGCTAGGTAT-5'
      /
      U*
      \
      TTGGACCACGTCGACTAGGGCTCCTCTGCGACCATA-3'

2.    TTCTGGTGCAGCTGATC-5'  TAGACGGCTAGGTATTA-5'
      /
      U*
      \
      TTGGACCACGTCGACTAGGGCTCCTCTGCGATCCATA-3'

3.    TTCTGGTGCAGCTGATC-5'  GAGGCGGCTAGGTATTAAA-5'
      /
      U*
      \
      TTGGACCACGTCGACTAGGGCTCCTCTGCGATCCATA-3'
```

B. Reaction Conditions

1. $^{32}$P Labeling of the Target Molecules

The five target molecules were labeled with $^{32}$P following a standard kinasing protocol. The labeled bands were isolated from the reaction solutions by denaturing PAGE (8 M. urea, 20% actylamide). $^{32}$P activity was determined by scintillation counting.

2. Capture Hairpin Immobilization on Microtiter Plates

A solution of the capture hairpin at 10 pmol/50 µl in PBS (150 mM NaCl, 10 mM phosphate, pH 7.2) was prepared. 50 µl/well was loaded on streptavidin-coated microtiter plates (Boehringer-Mannheim #1645692) and allowed to incubate for 30 min at room temperature. After the incubation period, the wells were washed 6 times with PBS, and blotted on clean Kimwipes.

3. General Procedure for Hybridization

A cocktail of the labeled targets was prepared by adding a sufficient amount of each target to the hybridization mixture to give a final concentration of ~20,000 cpm/target/25 µl. The final composition of hybridization mixture is 1 M NaCl, 10 mM phosphate, pH 7.2, and the specified concentration of the ligand. 25 µl of the target cocktail was loaded into each well and the plate was incubated for the specified amount of time. After incubation, each reaction mixture as quantitatively transferred to a 0.2 ml tube (Costar 6547).

The samples were analyzed by denaturing PAGE as follows: 10 µl of loading dye (8 M urea, 5 mM Tris-HC1, pH 7.5, 100 mM EDTA, 0.01% bromophenol blue, 0.01% xylene cynol) was added to the tube, and the whole sample was loaded onto a 15% acrylarnide/1.times.TBE/7 M urea gel. PAGE was run at 20 mA/gel for 2 hours. After electrophoresis, the gels were visualized by autoradiography.

4. General procedure for denaturation

The hybridization mixture was incubated typically for 2 hours, under the specified conditions (i.e., hybridization buffer+ligands). After incubation, the reaction mixture was removed, and the wells washed once with 100 µl 1M NaCl phosphate, pH 7.2. The plate was blotted on Kimwipes, and 50 µl of the specified denaturation buffer was added and allowed to incubate for the specified amount of time. The mixture was then quantitatively transferred to 0.2 µl of loading dye was added, and the sample analyzed by PAGE as above.

The autoradiograms were done by exposing X-ray films (Kodak X-OMAT) to the gels overnight, using an image intensifying screen. In some cases, there is a lane marked "control." This is a reference lane loaded with an equal volume (25 µl) of unhybridized target cocktail. Also, in each denaturation set of experiments, there is a lane marked "initial." This lane was loaded with the reaction mixture after hybridization, which indicates how much of the target has bound.

EXAMPLE 1

Effect of Single Ligands of Hybridization

An hybridization experiment was done where the following binders (see Table 1) were titrated: actinomycin D. distamycin A, ethidium bromide, and single-strand DNA binding protein (SSB). Incubation time was held constant at 2 hours. The results are shown in FIG. 1.

Results

1. Addition of actinomycin D to the hybridization reaction decreased the extent of hybridization in all cases. It acted as a single-strand binder (i.e., denaturant), with the activity proportional to the concentration.
2. Distamycin A improved binding up to a concentration of 0.016 mM, but did not improve binding (compared to the control with no ligands) at higher concentrations.
3. Ethidium bromide did not seem to affect the extent of hybridization up to a concentration of 0.001 mM, and it inhibited hybridization of the longer mismatches (19–21, 23-mer sequences) from a concentration of 0.004 mM and higher. There are no bands at 1 mM. However, there was a strong band at the top of the gel (data not shown).
4. SSB did not have an effect on the hybridization up to a concentration of 0.78 µg/well. However, a decrease in the extent hybridization was observed at the higher SSB concentrations.

EXAMPLE 2

Effect of a Ligand Combination of Hybridization

In this experiment, different combination of ligands were used. The titration of distamycin A was repeated (see above), and in three other sets, distamycin A concentration was fixed at 1 mM and the other ligands were titrated. The results are shown in FIG. 2.

Results

1. The distamycin A titration experiment showed nearly identical results with the first run. An improvement in the extent of hybridization was observed up to a concentration of 0.016 mM, with no improvement at higher concentrations.
2. Titration of actinomycin D in the hybridization mix with a constant amount of distamycin A showed markedly different results than when actinomycin D was used alone. A comparison of the two experiments (II-1 and III-2) showed that when actinomycin D was used alone, a decrease in the extent of hybridization was apparent even at the lowest concentration used (0.00025 mM). When actinomycin D was used in combination with distamycin A, a decrease in the extent of hybridization was noted at 0.004 mM or higher, an approximately 16-fold higher concentration.

3. A combination of distamycin A and ethidium bromide showed a similar effect While there was a decrease in the hybridization at >0.001 mM ethidium bromide when it was used alone, there was no decrease in hybridization when it was used in combination with distamycin A. Similar to the previous experiment, at 1 mM ethidium bromide, all the unhybridized target was noted at the top of the gel (data not shown).
4. Distamycin A apparently did not have an effect on the activity of SSB. The results of the distamycin A/SSB combination are similar to the results when SSB alone was titrated.

EXAMPLE 3

Effect of a Ligand Combination on Hybridization Time

The previous experiment showed that a combination of ligands (i.e., distamycin A and ethidium bromide) may improve the extent of DNA hybridization. A hybridization kinetics experiment was performed where the extent of hybridization in the absence of ligand (i.e., hybridization buffer only) and with a combination of ligands (1 mM distamycin A+1 µM ethidium bromide) were compared as a function of time.

Results

The results are shown in FIG. 3a. A comparison of the band intensities at 40 and 60 minutes shows an improvement in the hybridization in the presence of ligand. This trend is more clear when the intensities are measured (NIH Image) and plotted as shown in FIG. 3b.

EXAMPLE 4

Effect of Denaturation on Hybridization

In this set of experiments, we used various combinations of salt concentration, distamycin A, and the formamide (a denaturant), to control the extent of duplex to single-strand dissociation. The same set of molecules as in the previous section was used.

Hybridization of the target cocktail to the capture hairpin was carried out following the procedure described in General Methods. The final composition of the hybridization buffer was 1M NaCl, 10 mM phosphate, pH 7.2. The samples were incubated for approximately 2 hours at room temperature, and washed once with the hybridization buffer.

The denaturation buffer was 10 mM NaCl, 10 mM phosphate, pH 7.2, and NaCl tittered from 0 to 1M. The results are shown in FIG. 4. The amount of target dissociating from the capture hairpin decreased with an increase in the salt concentration with the 15-mer perfect match showing the greatest change.

Results

1. Salt Concentration Dependence of Denaturation

The wash buffer consisted of 40% formamide, 10 mM phosphate pH 7.2, and NaCl tittered from 0 to 1M. The results are shown in FIG. 4. The amount of target dissociating from the capture hairpin decreased with an increase in the salt concentration, with the 15-mer perfect match showing the greatest change.

2. Formamide and Distamycin A Concentration Effect on Dissociation

FIG. 5a shows a denaturation experiment where formamide was cross-tittered with distamycin A. The buffer concentration was kept constant at 10 mM NaCl, 10 mM phosphate pH 7.2 Formamide was tittered from 20–35% at 2.5 increments, while distamycin A was tittered from 0.062 mM to 1 mM in 4-fold increments. With no distamycin A, the stabilities of the mismatched targets increased, as shown by the decrease in their respective band intensities. This effect becomes more clear when the bands are quantified and plotted, as shown in FIG. 5b (with distamycin A independent variable), and in FIG. 5c (with formamide as the dependent variable).

3. Time Dependence of Dissociation as a Function of Distamycin A Concentration

An experiment was done where the extent of dissociation over time was measured as a function of distamycin A concentration in the wash buffer. The formamide concentration was kept constant at 40% (v/v), and distamycin A was tittered in 4-fold increments, at 0.062 mM, 0.25 mM, and 1 mM. Time points were from 0 (wash buffer was added and pulled out) to 60 min. The results are shown in FIG. 6. With 0–0.062 mM distamycin A, denaturation dissociate to the same extent as in the previous drug concentration. At 1 mM distamycin A, all target molecules show a lower extent of dissociation, with the perfect match showing a marked increase in stability.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed:
1. A method of identifying a nucleic acid molecule suitable for use in a probe for detecting the presence of one or more of a family of nucleic acid molecules, comprising the steps of:
   (a) providing the family of first nucleic acid molecules wherein each member of the family is related to all other members of the family by consensus sequence;
   (b) providing a second nucleic acid molecule having a sequence complementary to the consensus sequence; and
   (c) determining the ability of the second nucleic acid molecule to form a duplex with each member of the family in the presence of a first ligand known to affect duplex formation of nucleic acid molecules
   at a plurality of concentrations of the first ligand, wherein the nucleic acid molecule suitable for use in a probe is identified at a ligand concentration at which the second nucleic acid molecule has substantially the same ability to form a duplex with each member of the family.

2. The method of claim 1, further comprising the step of (e) repeating step (c) for a second ligand.

3. The method of claim 2, further comprising the step of (f) repeating step (c) in the presence of both first and second ligands.

4. The method of claim 1, wherein the second nucleic acid sequence has a sequence that has a homology less than a predetermined homology to other non-target partially complementary nucleic acid sequences.

5. The method of claim 2, wherein the first and second ligands are selected from the group consisting of actinomycin D, distamycin A, diminazane aceturate, bisbenzimide, and ethidium bromide.

6. The method of claim 1, wherein said first nucleic acid molecules of the family are at least a % homologous to each other, a being a number greater than 0 and less than 100, comprising the further steps of:
   (i) providing a third nucleic acid molecule which is no more than b % homologous to each of the first nucleic acid molecules of the family, where b is a number greater than 0 and less than a;
   (ii) determining the ability of the second nucleic acid molecule to form a duplex with the third nucleic acid molecule at a plurality of concentrations of the first ligand and identifying the second nucleic acid molecule as suitable for use in a probe when a ligand concentration is determined at which the ability of the second nucleic acid molecule to form a duplex with the third nucleic acid molecule is substantially different than its ability to form a duplex with each member of the family, and the ligand concentration is substantially equal to the ligand concentration determined in step (c).

7. The method of claim 6 wherein the ability of the second nucleic acid molecule to form a duplex with the third nucleic acid molecule is substantially less than its ability to form a duplex with each member of the family.

8. The method of claim 6, further comprising the step of repeating steps (e), (i) and (ii) for a second ligand.

9. The method of claim 8, further comprising the steps of repeating steps (c), (i) and (ii) in the presence of both the first and second ligands.

10. The method of claim 1 wherein each of the first nucleic acid molecules is selected from a group consisting of a genetic sequence of a first virus and variants thereof known to exist in nature.

11. The method of claim 6 wherein each of the nucleic acid sequences of the first nucleic acid molecules is selected from a genetic sequence of a first virus and variants thereof and the nucleic acid sequence of the third nucleic acid molecule is selected from a group of genetic sequences known to exist in nature exclusive of the first virus and the variants.

12. A method of detecting the presence or absence of a nucleic acid molecule suspected of being in a sample containing genetic material, the nucleic acid molecule being a member of a family of nucleic acid molecules that is related to all other members of the family by a consensus sequence, the method comprising:
   (a) providing the sample which potentially contains the nucleic acid molecule;
   (b) exposing the sample to a probe comprising a nucleotide sequence having a sequence complementary to the consensus sequence and identified according to the method of claim 1 as suitable for use in a probe, under conditions suitable for hybridization, in the presence of the ligand of claim 1 present at the concentration at which the nucleic acid molecule was identified as suitable for use in a probe; and
   (c) ascertaining the presence or absence of duplexed nucleic acid molecules comprising the probe, wherein the formation of the duplexed nucleic acid molecules indicates the presence of the nucleic acid molecule suspected of being in the sample.

13. The method of claim 12, comprising the further step of exposing duplex nucleic acid formed in step (b) to conditions suitable for amplifying the duplex.

14. A method of promoting the hybridization of a nucleic acid capture moiety to a target single-stranded nucleic acid sequence and all its family members without hybridizing to a plurality of other non-target partially complementary nucleic acid sequences present in a sample, the steps comprising:
   (a) providing:
      (i) a nucleic acid capture moiety comprising the nucleic acid molecule identified according to the method of claim 5;
      (ii) the sample containing the target nucleic acid sequence or any of its family members, wherein the sample has been treated such that all duplex nucleic acid sequences present in the sample are rendered single-stranded; and
      (iii) a nucleic acid sequence binding ligand used to identify the nucleic acid molecule provided in step (a)(i); and
   (b) forming a reaction mixture comprising the nucleic acid capture moiety, the sample and the nucleic acid sequence binding ligand under conditions such that the nucleic acid sequence binding ligand promotes hybridization of the target single-stranded nucleic acid sequence and all its family members to the nucleic acid capture moiety without promoting hybridization of the nucleic acid capture moiety to other non-target partially complementary nucleic acid sequences.

15. The method of claim 14 wherein the nucleic acid sequence binding ligand is selected from the group consisting of: a compound which binds to a duplex nucleic acid in a sequence-specific way; a compound which binds to a duplex nucleic acid in a non-specific way; a protein; an enzyme; an enzyme which alters the structure of a duplex nucleic acid to which it binds; an enzyme which alters the structure of a duplex nucleic acid to which it binds by breaking or forming a covalent or non-covalent bond, between an atom of the nucleic acid and another atom; an enzyme which cleaves one or both strands of a duplex nucleic acid to which it binds; a restriction enzyme; a restriction endonuclease; an enzyme which methylates the duplex to which it binds; an enzyme which alkylates the duplex nucleic acid to which it binds; a nucleic acid ligase such as DNA ligase, an enzyme which promotes or catalyzes the synthesis of nucleic acid; a nucleic acid polymerase; a nucleic acid polymerase which requires a double stranded primer; a DNA polymerase; DNA polymerase I; Taq polymerase; an RNA polymerase; an enzyme which alters the primary or secondary structure of a duplex nucleic acid to which it binds; a topoisomerase; an enzyme which promotes or inhibits recombination; a DNA binding agent; a mutagen; a compound which enhances the expression of a gene under the control of the duplex bound by a ligand; a compound which intercalates into a duplex nucleic acid molecule; a compound which, when contacted with a reaction mixture comprising a first single stranded nucleic acid molecule and a second single stranded nucleic acid molecule will increase the free energy of duplex formation at least n-fold, wherein n is 2, 5, 10, 50, 100, 500, $10^3$, $10^4$, $10^5$, or $10^6$, a compound which, when contacted with a reaction mixture will decrease the free energy of duplex formation by at least n-fold, wherein n is 2, 5, 10, 50, 100, 500, $10^3$, $10^4$, $10^5$, $10^6$.

16. The method of claim 15, wherein the nucleic acid sequence binding ligand further comprises a single-stranded nucleic acid binding ligand.

17. The method of claim 15, wherein the nucleic acid sequence binding ligand further comprises a duplex nucleic acid sequence binding ligand.

18. The method of claim 15, wherein the nucleic acid sequence binding ligand further comprises a nonspecific nucleic acid binding ligand.

19. The method of claim 15, wherein the duplex nucleic acid sequence binding ligand is selected from the group consisting of actinomycin D, distamycin A, diminazene aceturate, bisbenzamide, and ethidium bromide.

20. The method of claim 14 wherein the target nucleic acid sequence and all its family members comprise a region of a viral nucleic acid sequence.

21. The method of claim 20, wherein the region of viral nucleic acid comprises a region of the AIDS virus.

22. The method of claim 14, wherein the target nucleic acid sequence and all its family members comprise a region of an oncogene.

23. The method of claim 22, wherein the oncogene is selected from the group consisting of p53, ras, BRCA1, and BRCA2 and each of their family members.

24. The method of claim 14, wherein the target sequence and any of its family members are amplified by PCR prior to step (a)(ii).

* * * * *